United States Patent [19]

McVicker et al.

[11] 4,141,817

[45] Feb. 27, 1979

[54] HYDROCARBON CONVERSION PROCESSES UTILIZING A CATALYST COMPRISING A GROUP VIII NOBLE METAL COMPONENT SUPPORTED ON GROUP IIA METAL OXIDE-REFRACTORY METAL OXIDE SUPPORTS

[75] Inventors: Gary B. McVicker, Westfield, N.J.; Robert L. Garten, Cupertino, Calif.

[73] Assignee: Exxon Research & Engineering Co., Florham Park, N.J.

[21] Appl. No.: 906,994

[22] Filed: May 18, 1978

Related U.S. Application Data

[63] Continuation-in-part of Ser. No. 729,834, Oct. 4, 1976, Pat. No. 4,094,821, which is a continuation of Ser. No. 579,789, May 22, 1975, abandoned.

[51] Int. Cl.² .............................................. C10G 35/08
[52] U.S. Cl. ..................................... 208/139; 208/138; 252/442; 252/455 R; 252/473; 252/466 PT
[58] Field of Search .............................. 208/138, 139; 252/466 PT, 473, 442, 455 Z, 455 R

[56] References Cited

U.S. PATENT DOCUMENTS

| | | | |
|---|---|---|---|
| 3,376,215 | 4/1968 | Bertolacini et al. | 208/138 |
| 3,397,137 | 8/1968 | Pickert et al. | 208/138 |
| 3,846,282 | 11/1974 | Hayes | 208/139 |
| 3,951,782 | 4/1976 | Buss | 208/139 |

*Primary Examiner*—C. Davis
*Attorney, Agent, or Firm*—Joseph J. Allocca; R. J. Baran

[57] ABSTRACT

The instant invention relates to a novel catalyst which comprises a physical mixture of (1) at least one catalytically active transition metal selected from Group VIII of the Periodic Table of the Elements in combination with at least one alkaline earth metal oxide, and (2) an acidic refractory oxide. The combination of one or more of said Group VIII metals and one or more alkaline earth metal oxides may be provided by supporting said metals and said oxides on a nonacidic refractory oxide support. These catalysts are useful in hydrocarbon conversion processes and are characterized as having improved stability under oxidizing conditions, for example, the high temperature oxidation treatments encountered in regenerating deactivated reforming catalysts.

8 Claims, 3 Drawing Figures

HYDROCARBON CONVERSION PROCESSES UTILIZING A CATALYST COMPRISING A GROUP VIII NOBLE METAL COMPONENT SUPPORTED ON GROUP IIA METAL OXIDE-REFRACTORY METAL OXIDE SUPPORTS

CROSS REFERENCE TO RELATED APPLICATIONS

This application is a continuation-in-part of Ser. No. 729,834 filed Oct. 4, 1976, now U.S. Pat. No. 4,094,821, which is a Rule 60 Continuation of Ser. No. 579,789 filed May 22, 1975, now abandoned.

FIELD OF THE INVENTION

The instant invention relates to a novel catalyst which comprises a physical mixture of (1) at least one catalytically active transition metal selected from Group VIII of the Periodic Table of the Elements in combination with at least one alkaline earth metal oxide, and (2) an acidic refractory oxide. The combination of one or more said Group VIII metals and one or more alkaline earth metal oxides may be provided by supporting said metals and said oxides on a nonacidic refractory oxide support. These catalysts are useful in hydrocarbon conversion processes and are characterized as having improved stability under oxidizing conditions, for example, the high temperature oxidation treatments encountered in regenerating deactivated reforming catalysts.

In one much preferred embodiment, iridium combined with a Group IIA metal oxide selected from the group consisting of calcium oxide, barium oxide and strontium oxide, is supported on deacidified alumina, which functions to hold the iridium and the Group IIA metal oxide combination in intimate contact during regeneration of the catalyst. An acidic component is admixed with the nonacidic iridium-Group IIA oxide-deacidified alumina component to produce an overall acidic catalyst. The acidic component is preferably a halogen treated alumina, for example, a chlorine treated alumina. The resulting physically mixed bifunctional catalyst is useful in reforming operations and may be periodically regenerated by burning in air to remove carbonaceous deposits, without agglomerating the iridium as large crystallites.

BACKGROUND OF THE PRIOR ART

It is known in the art that noble metals supported on deacidified alumina are useful for dehydrogenation operations. The deacidified alumina may be prepared by combining the alumina with a Group IIA metal oxide. Examples of these catalysts and their uses may be found in U.S. Pat. No. 2,478,916, U.S. Pat. No. 3,759,823, U.S. Pat. No. 3,696,167 and U.S. Pat. No. 3,763,255. Because all of these patents disclose a hydrocarbon dehydrogenation process, there is no teaching that the catalysts may be physically mixed with an acidic oxide material and that said admixture is useful in hydrocarbon conversion processes requiring an acidic function in the catalyst, e.g., reforming, hydrocracking, isomerization. In fact, the presence of even a small amount of acidity adversely affects the yield of the desired olefinic products produced by a nonacidic dehydrognation catalyst.

Furthermore, in the above patents, the Group IIA metal oxide is used only to neutralize the acidic support. Thus, the equivalency of magnesium oxide, for example, with the other Group IIA metal oxides is clearly taught.

In the catalyst of the instant invention, the Group IIA metal oxide is utilized to stabilize the catalyst under severe oxidation conditions. The Group IIA metal oxide is selected so as to combine with the transition metal under oxidizing conditions and form a complex oxide of the Group IIA metal and Group VIII metal. The complex metal oxide is stable to further oxidation and prohibits the growth of large Group VIII metallic or Group VIII oxide or complex oxides crystallites. Thus, in the catalyst of the instant invention, the Group IIA metal oxides, except for magnesium oxide may be used as supports for each of the Group VIII transition metals since complex oxides are formed between these components under oxidizing conditions. Similarly, Group IIA metal oxides, except for magnesium oxide, may be supported on a high surface area refractory oxide, such as silica or alumina in an amount sufficient to (1) neutralize the acidity of the support, if any, and (2) provide an excess to combine with the Group VIII metal. The resulting alumina-Group IIA oxide support stabilizes the Group VIII metals under oxidation conditions. When the Group VIII transition metal is platinum, magnesium oxide may be used as well as the other Group IIA metal oxides in a manner as described above, since platinum is known to form a complex oxide under oxidation conditions with magnesium.

As noted above, when the Group IIA metal is supported on an acidic refractory oxide, such as alumina, a portion of the Group IIA oxide equivalent to the acidity of the alumina is used to neutralize the acidity of the support. In this function, all the Group IIA oxides are equivalent since all will neutralize the acidity present on an acidic refractory oxide support. However, an excess amount of Group IIA oxide over and above that required to neutralize the support is necessary to combine with and stabilize the Group VIII metal under oxidizing conditions. It is this excess that must be capable of combining with the Group VIII metal to produce a complex oxide. In short, for the reasons given above, the Group IIA metal oxides are not equivalent when used to form the catalysts of the instant invention.

The use of Group IIA metal oxides as catalyst supports is taught, in passing, in various patents, for example, see U.S. Pat. No. 2,911,357 which teaches that multimetallic catalysts which include Group VIII metals may be supported on magnesium oxide. However, there is no teaching that these magnesium supported catalysts may be further mixed with an acidic inorganic oxide to provide a catalyst mixture having the acidity required by many hydrocarbon conversion processes including hydrocracking, reforming, etc.

In U.S. Pat. No. 3,789,020 a catalyst comprising a physical mixture containing more than one metal supported on an inorganic refractory oxide support and an additional inorganic oxide support material having no metal supported thereon is taught. The purpose, patentees point out, for preparing the catalyst in this manner, is that they wish to maximize alloy formation on that portion of support containing the metal. Thus, the patentees support the noble metals on a small portion of the total support, for example, one-tenth, and treat this portion of the support under reducing conditions to form the alloy. This portion is then mixed with additional support material to provide a physical mixture wherein the amount of noble metal is at an economical level, for example, less than about 1% by weight. Thus, in effect, the patentees' addition of the excess support material is to provide dilution of the expensive catalyst metals. See also U.S. Pat. No. 3,346,510 wherein the patentees physically admix an acidic refractory oxide with a nonacidic supported Grp. VIII noble metal catalyst to prepare a bifunctional catalyst. The patentees, however, do not teach, show or suggest the use of a Group IIA metal oxide to stabilize the noble metal from agglomeration under high temperature oxidizing conditions.

SUMMARY OF THE INVENTION

Figure 1:
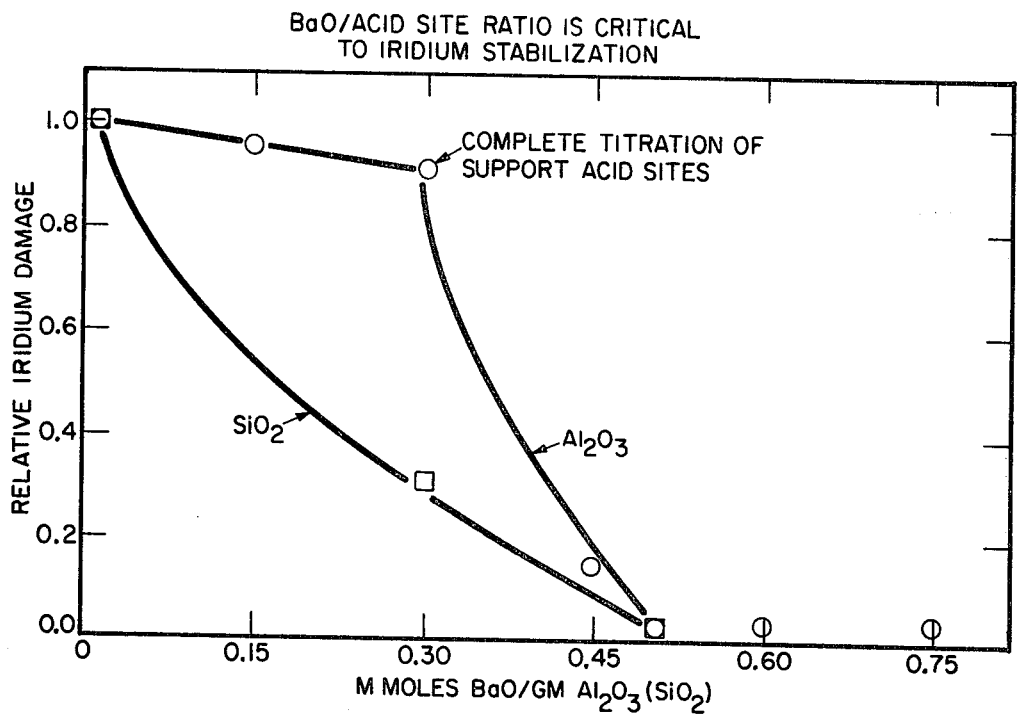
FIG. 1 represents the criticality to iridium stability of the BaO/Acid Site ratio.

This invention relates to novel catalysts which comprise a physical mixture of (1) at least one transition metal selected from Group VIII of the Periodic Table of the Elements in combination with at least one Group IIA metal oxide, said Group IIA metal oxide being selected so as to form a complex oxide with said transition metal under oxidizing conditions and (2) an acidic refractory oxide. In one embodiment of the instant invention the transition metal and the alkaline earth metal oxide are both supported on the surface of a nonacidic refractory oxide support material. As used throughout the specification, the terms inorganic refractory oxide and nonacidic refractory oxide do not include the alkaline earth metal oxide which combines with the Group VIII metal in the complex oxide.

The catalyst of the instant invention are useful hydrocarbon conversion catalysts and may be used in reforming, hydrocracking, and hydroisomerization reactions. These catalyst materials are characterized as having greatly improved stability under oxidizing conditions for reasons that will further be explained below. Thus, the use of the novel catalysts of the instant invention in processes, such as reforming, wherein during use, the catalyst becomes deactivated by the deposition of carbon from the hydrocarbon feed stream onto the active sites of the catalyst and said carbon is removed by burning in oxygen, will be appreciated by one skilled in the art.

In the catalysts of the instant invention, the transition metal will be selected for functioning in the process of choice, for example, Group VIII noble metals, such as platinum, iridium, palladium, ruthenium, and rhodium are useful in reforming processes and thus the skilled artisan will design a reforming catalyst by including at least one member of this group. In a reforming catalyst, a very much preferred catalyst will include platinum or iridium, or a combination of both.

The nonnoble metals of Group VIII, for example, iron, nickel and cobalt, are useful hydrogenation catalysts and can also be used in ammonia synthesis. Thus, the skilled artisan when designing a catalyst for use in these processes would choose a catalyst metal from this group.

Additionally, the Group VIII metals, described above, may be combined with additional metals which act as catalyst promoters. These promoter metals do not necessarily have to be capable of combining with a Group IIA metal oxide to form a complex oxide since, in general, the promoter metals are more stable in their promoting function then the transition metal in its catalyst function when subjected to a regeneration step. Promoter metals which can be combined with Grp. VIII noble metal catalysts for reforming processes include Grp IB metals, for example, silver, copper and gold; Group IIB metals, for example, zinc, cadmium; Group VIB metals, e.g. Mo, W; Group VIIB metals, e.g. manganese, rhenium; etc., and other promoter metals, lead, indium, etc. Specifically, see U.S. Pat. No. 3,617,518, 3,729,408, and 3,769,201, wherein it is taught that Group IB metals are desirably included in a Group VIII metal reforming catalyst to decrease the hydrogenolysis (cracking) activity thereof.

The amount of Group VIII metal provided in the novel catalysts of the instant invention will vary with intended use and economics, for example, in a reforming catalyst wherein a Grp VIII noble metal is used the total catalyst metal is desirably maintained at less than 2% by weight of the total catalyst, more preferably less than 1%, e.g. 0.01 to 2 weight %, more preferably from 0.05 to 1 weight %. When the catalyst of the instant invention includes a Group VIII nonnoble metal, large amounts may be used, for example, from 1 to 25 weight % of nickel may be used in a hydrogenation catalyst.

Based on the molar amount of Group VIII metal or metals present, the catalysts of the instant invention also contain a substantially equivalent or greater molar amount of a Group IIA metal oxide capable of combining with said Group VIII metal in a complex oxide. It is to be understood that this molar quantity of Group IIA oxide is over and above any Group IIA oxide required to neutralize acidity which may be present on the inorganic refractory support when employing a supported Group IIA oxide. Of course, when a Group IIA metal oxide itself is utilized as a support material a sufficient amount of Group IIA metal is necessarily present.

As stated above, it is believed that the function of the Group IIA metal oxide is to combine with the Group VIII metal under oxidizing conditions and form a complex oxide of said Group IIA metal and said Group VIII metal. The formation of this complex oxide acts to prevent the agglomerization of the Group VIII metal into large crystallites under oxidizing conditions. Upon subsequent reduction, the complex oxide is converted into a high surface area Group VIII metal, having necessarily high catalytic activity and regenerates the Grp IIA oxide. The commercial significance of this behavior may be appreciated by referring to U.S. Pat. No. 3,147,229, wherein the importance of maintaining a high metal surface area in reforming catalysts is taught. Thus, at least an approximately equivalent amount of the Group IIA transition metal oxide, which combines with the metal to form the complex oxide, must be present in the catalyst. The amount of Group IIA metal oxide in the supported catalysts of the instant invention is preferably from 0.5 to 50 moles per mole of the Group VIII metal, more preferably the Group IIA metal oxide will be present at a level of from about 0.8 to 20 moles per mole of said Group VIII metal or metals.

In the embodiment of the instant invention wherein the Group IIA metal oxide is utilized as a support for the noble Grp VIII metal or metals it is necessary that a Group IIA metal oxide having sufficiently high surface area to give catalysts of adequate activity be used. Preferably, the Group IIA metal oxide will have a surface area of from 0.1 to 100, more preferably from 1.0 to 100 m$^2$/g, as measured by the BET(Branauer-Emmett-Teller) method for determining surface area. High surface area Group IIA metal oxides are known articles of commerce or can easily be synthesized by the skilled artisan.

When it is desired to support both the Group IIA metal oxide and the Group VIII metal on an inorganic refractory oxide it is also desirable to have a high surface area form of the inorganic refractory oxide, e.g., from about 50 to 600 m$^2$/g. In general, inorganic refractory oxides selected from Group III and IV of the Periodic Table of the Elements are preferred supports, for example, silica, silica-alumina, (including natural and synthetic zeolites) and alumina. It is critical that said inorganic refractory oxide be a nonacidic material. Certain of these materials, for example, silica, are essentially nonacidic as procured in commerce, however, numerous refractory oxides, such as alumina and silica-alumina, must be treated to remove the acidity, i.e. by neutralization with a basic material, e.g., alkaline hydroxides such as KOH, NaOH, etc. Thus, when a nonacidic refractory oxide, such as silica is used, the Group VIII metal and the Group IIA metal oxide can be supported on said silica by methods known in the art. For example, solutions, preferably aqueous solutions of the precursors of the Group VIII metal and the alkaline earth metal oxide may be contacted, either simultaneously or serially, with silica under impregnating conditions, although in sequential impregnation, it is preferred to impregnate the Group IIA metal precursor first. In this preferred, sequential technique, the refractory oxide support impregnated with a Group IIA metal precursor is dried to remove excess solvent, e.g. at a temperature of from about 50°-150° C., then calcined under an oxygen containing atmosphere at a temperature sufficiently high enough to produce a surface Grp IIA oxide on the refractory oxide support (calcination temperatures of 200°-700° C.). The calcined Grp IIA metal oxide containing support is then impregnated with the appropriate Grp VIII metal precursor, dried, and reduced to form an active (supported Grp IIA metal oxide-Grp VIII metal) catalyst.

When the catalysts of the instant invention are prepared by simultaneously impregnating the precursors for the Group IIA metal oxide and the Group VIII metal onto a nonacid support such as silica, the following catalyst preparation scheme is preferred.

The impregnated catalyst is dried at a low temperature, e.g, 50° to 150° C. for a time sufficient to substantially remove the excess solvent. The impregnated dried catalyst is then calcined by contacting with an atmosphere comprising from 0.2 to 100% by volume oxygen at a temperature of from 200° to 700° C. for a period of time sufficient to convert the Group IIA precursor into the oxide and form the surface Grp. IIA-Group VIII metal complex oxide, Finally, the calcined catalyst is reduced, e.g., in hydrogen, at a temperature of from 200° to 700° C. for a period of time sufficient to form an active catalyst, i.e. convert Group VIII metal to the metallic state. At this point, the Group IIA metal will be present as the oxide, which has very little, if any, catalytic effect, and thus will not substantially affect the properties of the catalysts of the instant invention. Suitable precursors include water soluble salts of said Group VIII metals, for example, the nitrates, nitrites, carbonates, acetates, and formates, etc. of cobalt, iron or nickel; chloroiridic acid, iridium tribromide, ammonium chloroiridate, chloroplatinic acid, ammonium chloroplatinate, platinum or iridium amine salts, palladium trichloride, ruthenium tribormide, rhodium trichloride, etc. Sutiable precursors for the Group IIA metal oxide include nitrate, nitrite, formate, acetate, oxide and propionate salts. The use of Group IIA chloride salts must be avoided as they are strong fluxing agents and do not readily form the corresponding oxide. The above precursors are all soluble in water and are preferred since aqueous impregnation techniques are generally more suitable in the preparation of the above catalysts. It is, however, noted that nonaqueous techniques may be used if suitable precursors, which are soluble in the nonaqueous solvents, are known. Metal carbonyls, amines, phosphines, and acetylacetonates may be used in nonaqueous impregnating solutions. It is noted that whether simultaneous or sequential techniques are used in preparing the above described catalysts, the amounts of Group IIA metal oxide or Group VIII metal precursors will be adjusted to give the required ratios described above for the final catalysts.

In another embodiment of the instant invention, it has been discovered that prior art, agglomerated catalysts, e.g., noble metals such as platinum, iridium and rhodium, etc., supported on alumina, may be redispersed by impregnating a suitable amount of a precursor of Group IIA metal oxide capable of forming a complex oxide with the metal of said agglomerated catalyst onto said agglomerated catalyst, and calcining said impregnated catalyst at an elevated temperatures, e.g., at least 400° C., preferably from 500° to 800° C., in the presence of oxygen for a time sufficient to substantially convert said metal into a metal Group IIA metal complex oxide. The calcined catalyst is then activated by reducing said complex oxide, e.g., in hydrogen to contain a catalyst comprising the metal in a nonagglomerated, i.e. highly dispersed state.

When an acidic inorganic oxide support material is used to support the Group VIII metal and the Group IIA metal oxide, it is necessary to neutralize the acidity prior to the above-described impregnation procedure or to provide sufficient Group IIA metal precursor in the impregnating solution to neutralize the acidity of the support material and have an additional amount left over to combine with the Group VIII metal in the subsequent forming of the complex oxide. In this embodiment, alumina may be used as the refractory oxide support. The acidic alumina may first be contacted with sufficient basic material to neutralize the acid sites present in the alumina and form a deacidified alumina which can then be impregnated with a Group VIII precursor, dried, calcined, and reduced to form an active catalyst in the manner described above for silica.

In a much preferred impregnation technique of the instant invention, certain Group VIII transition metal complexes can be reacted with an excess of Group IIA metal oxide precursor in an aqueous solution. The resulting complex salt plus excess Group IIA metal oxide precursor can be used to impregnate the inorganic oxide supports described above. For example, it has been found that barium nitrite can be reacted with chloroplatinic acid or chloroiridic acid or both, to yield an impregnating species comprising both barium and platinum and/or iridium in a complex salt. As further described below, this technique is especially preferred for preparing the catalyst of the instant invention, when a platinum-iridium bimetallic catalyst is desired. Platinum-iridium bimetallic catalysts prepared in this manner have unexpectedly been found to have improved stability to multiple regenerations as compared to catalylsts prepared by coimpregnating platinum and iridium onto an alumina supported barium oxide.

The active Group IIA oxide-Grp VIII metal catalysts are then physically mixed with an acidic inorganic refractory oxide to provide the novel catalysts of the instant invention. An acidic function is necessary in catalysts used in the various hydrocarbon conversion processes in which it is desired to use the catalysts of the instant invention. The acidic inorganic refractory oxide may be selected from the group consisting of alumina halogen-treated alumina and silica-alumina, including both zeolites and amorphous silica alumina. In general, the ratio by weight of the acidic inorganic refractory oxide to the active Group IIA oxide - Group VIII metal catalyst will vary from 0.1 to 20, preferably from 1 to 10. The acidic inorganic refractory oxide may be mixed with the Group IIA oxide-Group VIII metal cataylst by techniques known in the art for blending of solids, for example, ball milling the dry powders, or slurry techniques.

The novel catalysts of the instant invention may also be provided by forming the acidic inorganic refractory oxide as a gel from a solution containing a suitable precursor for said acidic inorganic refractory oxide and said Group IIA-Group VIII metal catalyst as a slurry. In this form, the acidic inorganic refractory oxide will comprise a continuous phase surrounding active Group IIA oxide- Group VIII metal catalyst particles. However, this embodiment is a physical mixture within the scope of this invention.

The acidic inorganic refractory oxide may be mixed with the nonacidic Group IIA oxide-Group VIII metal catalyst at any time subsequent to the drying of the impregnated support. For example, the nonacidic Group II oxide-Group VIII metal catalyst may be calcined and then admixed with the acidic refractory oxide support material and the admixture contacted with a reducing agent to activate the catalyst by converting the complex oxide to the metal or the Group IIA oxide-Group VIII metal catalyst may be reduced, and then admixed with the acidic refractory oxide.

The novel catalysts of the instant invention are especially useful in hydrocarbon conversion processes, e.g., reforming, where it becomes necessary to regenerate the catalyst from time to time by removing the carbon deposited thereon during said process. The catalyst is burned in an oxygen containing atmosphere at conditions wherein the carbon is removed as the oxides thereof. Generally, regeneration processes will be carried out at temperatures of from 300° to 600° C., however, higher temperature excursions produced by uncontrolled burning rates are known in regeneration processes. At the above temperatures and at oxidizing conditions the prior art catalyst metals, e.g., the noble metals and especially iridium, tend to agglomerate and form large crystallites of the corresponding oxides and/or metals. Large oxide crystallites often are difficult to reduce back to the metal (which is generally the desired form for catalytic activity) and even after reduction are not of sufficient surface area to provide the desired catalytic activity. It is known in the art that these materials may be activated by treating with a halogen containing gas, for example, see U.S. Pat. No. 3,134,732, wherein chlorine treating processes for the redispersion of agglomerated noble metal catalysts are described. However, it would be desirable to eliminate this chlorine treating process, that is, it would be desirable, to have a catalyst which under oxidizing conditions did not form large metal or metaloxide crystallites.

It is found upon reduction of the regenerated catalysts of the instant invention that the original catalytic activity and surface area is maintained and thus a chlorine redispersion step is not necessary.

The above-described behavior of the Group IIA-Group VIII metal catalysts of the instant invention may be exemplified by the following reaction schemes:

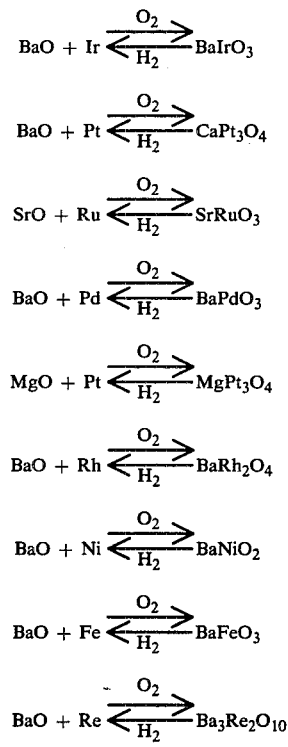

The reaction to the right occurs during the regeneration of the catalyst after use, as, for example, in the regeneration of reforming catalysts by burning off carbon deposits. The reaction to the left takes place upon reduction to activate the regenerated catalyst.

The preferred support material for preparing a reforming catalyst is alumina and the preferred method for preparing a reforming catalyst comprises contacting the alumina, at impregnating conditions, with an aqueous solution containing the precursor of one or more Group VIII noble metals, for example, chloroiridic acid, chloroplatinic acid, iridium tribromide, ammonium chloroiridate, ammonium chloroplatinate, platinum and/or iridium amine salts, palladium trichloride, ruthenium tribromide, rhodium trichloride, etc., and a sufficient amount of a Group IIA metal oxide precursor to neutralize the acidic sites present in alumina and an additional amount to combine with the Group VIII noble metal to form a complex oxide. The impregnating solution may contain from 0.01 to 1.0 g/ml noble metal, preferably from 0.1 to 0.5 g/ml calculated as the metal, and from 0.01 to 1.0 g/ml, preferably from 0.1 to 0.5 g/ml, of the Group IIA metal oxide precursor calculated as the metal. The impregnated catalyst will comprise from about 0.1 to 10 wt. % noble metal, and from about 0.1 to 20 wt. % Group IIA metal based on total impregnated catalyst (dry) weight. The impregnated catalyst is then dried at a temperature of from about 50 to 150° C. for a time sufficient to remove the excess water, then calcined by contacting with oxygen, e.g., an atmosphere comprising from 0.2 to 100 volume % oxygen, with or without an inert diluent, e.g., He or $N_2$, at a temperature of from 200 to 700° C. and a pressure of from 0.1 to 100 atmospheres for a time sufficient to produce a surface phase Group IIA-Group VIII complex oxide. The calcined catalyst may or may not be activated by reducing at this point. The calcined or reduced catalyst is then admixed with a halogen treated alumina, for example, an alumina containing up to 1% by weight added chlorine to produce the novel catalyst of the instant invention, i.e. comprising from 0.1 to 1% by weight Group VIII noble metal based on the total catalyst weight. The novel catalyst must be activated after admixing if a reducing step was not previously carried out; however, the novel catalyst of the instant invention may be activated in situ by contacting with a hydrocarbon feedstream in the presence of hydrogen at reforming conditions. For example, the novel catalyst of the instant invention, whether activated or not, may be contacted with a naphtha feedstream comprising paraffins, naphthenes and aromatics, boiling at from 35° 300° C., at a temperature of from 300° to 600° C. and a pressure of from 15 to 500 psig. Hydrogen at a rate of from 1,000 to 10,000 standard cubic feet per barrel is also contacted with the catalyst and the naphtha feedstream. The naphtha is contacted with the catalyst for a time sufficient to reform the naphtha into a higher octane product, e.g., at 0.2 to 20 weight feed charged per hour per unit weight of catalyst. After a certain on-stream time, for example, 1,000 hours, the catalyst will be deactivated by deposition of carbon on the active sites. The catalyst is then removed from contact with the naphtha feedstream and treated with an oxygen-containing gas, for example, air, at a temperature of at least 400° C., preferably from 450° to 550° C., for a time sufficient to remove the carbon. This oxygen treated catalyst may then be reduced by contacting with hydrogen at a temperature of from 200° to 700° C. and a pressure of from 15 to 500 psig for a time to substantially reduce all the Group IIA-Group VIII complex oxide to the Group VIII metallic state. The catalyst is then put onstream, that is, it is again contacted with the naphtha at the above conditions, and it is found that the activity is substantially equivalent to the original catalyst activity, i.e., before regeneration.

It should be noted that after several regenerations it may be necessary to replace chlorine on the acidic support, which has been removed during catalyst regeneration.

The catalytic materials previously described find use in catalytic processes other than just reforming. The materials are useful for the catalytic hydrogenation of benzene to cyclohexane (i.e. aromatics to cyclic aliphatics), as steam reforming catalysts, for the catalytic decomposition of hydrazines, as catalysts for the reduction of $NO_x$ under lean conditions, as combustion promoters for cat cracking catalysts, for the catalytic oxidation of $SO_2$ to $SO_3$, for the catalytic dehydrogenation of alcohols to ketones, for the hydrogenation of dextrose to sorbitol.

The following are specific embodiments of the instant invention:

Preparation of Catalysts

EXAMPLE 1 — Group IIA Metal Oxide/$Al_2O_3$ Supports

A catalyst support containing 7.9% BaO on alumina was prepared as follows: 1.29 g of $Ba(NO_2)_2 \cdot H_2O$ was dissolved of 6.0 ml of distilled water. This solution was used to impregnate 9.3 g of $\eta$-$Al_2O_3$ (BET surface area of 217 m$^2$/g). The impregnated support was dried at 140° C. under flowing air for 5.0 hours. After the initial drying, the support was calcined at 600° C. for 16 hours under flowing air to ensure complete decomposition of $Ba(NO_2)_2 \cdot H_2O$ into a BaO surface phase. The loading level of BaO corresponds to 0.52 mmoles BaO/g of support.

By a similar procedure, the oxides of Ca, Sr and Mg were placed on an $\eta$-$Al_2O_3$ support, using aqueous nitrate salt solutions as the oxide precursors. In each case the Group IIA metal oxide loading level was 0.52 mmoles Group IIA metal oxide/g of support.

Since the Group IIA oxides are basic, it was imperative to ascertain if residual acidity remained on the $\eta$-$Al_2O_3$ support (this $\eta$-$Al_2O_3$ possessed 0.30 ± 0.05 mmoles acid sites/g as measured by $\eta$-butylamine titration). As shown in Table I, the oxides of Ba, Ca and Sr completely titrate the acidic sites of the $\eta$-$Al_2O_3$ carrier.

Table I

Properties of 0.52 mmole Group IIA oxide/ $\eta$-$Al_2O_3$ Mixed Oxide Supports

| Group IIA Oxide | Wt. % | Acidic[a] | Surface Area[b] (m$^2$/g) |
|---|---|---|---|
| None | — | Yes | 217 |
| BaO | 7.1 | No | 209 |
| CaO | 2.1 | No | 218 |
| MgO | 1.3 | Yes | 213 |
| SrO | 4.6 | No | 221 |

[a]Determined by $\eta$-butylamine titration using a series of Hammett indicators
[b]BET surface area This indicates that the oxides of Ba, Ca and Sr are well dispersed over the $\eta$-$Al_2O_3$ surface. The oxide of Mg did not completely neutralize the acid sites of the $\eta$-$Al_2O_3$ support. This result suggests that the MgO phase is not well dispersed over the $\eta$-$Al_2O_3$ surface and further suggests the possible formation of a surface, $MgAl_2O_4$, spinel.

The BET surface areas of the Group IIA metal oxide/$Al_2O_3$ supports was found to be comparable with that of the starting $\eta$-$Al_2O_3$.

EXAMPLE 2 — Iridium Catalysts

A series of 2% iridium (0.104 mmoles Ir/g) catalysts were prepared on the 0.52 mmole Group IIA metal oxide/$\eta$-$Al_2O_3$ supports as follows: 1.1 ml of a standard chloroiridic acid solution (0.091 g Ir/ml) was diluted to 3.0 ml with distilled water. Four such solutions were used to impregnate 4.9 g of the Group IIA metal oxide/$\eta$-$Al_2O_3$ supports described in Table 1. The iridium impregnated catalysts were dried at 120° C. for 16 hours under flowing air. The resulting catalysts possess a Group IIA metal oxide to iridium mole ratio of 5. To test the oxidative stability of the Group IIA metal oxide-iridium catalysts, the catalysts were subjected to the following treatment. The catalysts were reduced at 500° C. for 2 hours with 20% $H_2$ in He (500 cc/min) and then calcined with 20% $O_2$ in He (500 cc/min) at 500° C. for 4.0 hours. The ability of the Group IIA metal oxide doped $\eta$-$Al_2O_3$ carriers to retard the agglomeration of iridium under oxidizing conditions was compared against a 2% iridium/$\eta$-Al$_2$O$_3$ catalyst. The basis of comparison was quantitative x-ray diffraction measurements. Agglomeration of iridium is indicated by the appearance of IrO$_2$ diffraction lines in the x-ray pattern. The diffraction lines of $\eta$-Al$_2$O$_3$ were employed as an internal standard in the individual catalysts. The results of the oxidation tests are summarized in Table II.

Table II

Oxidation[a] Studies of 2% Iridium Catalysts Supported on Group IIA Metal Oxide/$\eta$-Al$_2$O$_3$ Supports Group IIA metal oxide/iridium mole ratio = 5

| Group IIA Metal Oxide | Relative Agglomeration[b] as IrO$_2$ (%) | Known Complex Oxide |
|---|---|---|
| None | 100 | — |
| BaO | 0.0 | BaIrO$_3$ |
| CaO | 0.0 | CaIrO$_3$ |
| MgO | 100 | None |
| SrO | 0.0 | SrIrO$_3$ |

[a] Catalysts were pre-reduced with 20% H$_2$ in He at 500° C. for 2.0 hours and then oxidized at 500° C. under 20% O$_2$ in He for 4.0 hours.
[b] Determined by comparative x-ray diffraction measurements.

It is seen that the oxides of Ba, Ca and Sr completely suppress the oxidative agglomeration of iridium. Since the oxides of Ba, Ca and Sr are well known to form iridates, the mode of oxidative stabilization is presumably via the formation of a stable complex oxide, e.g., BaIrO$_3$, CaIrO$_3$, SrIrO$_3$, surface phase. The inability of The inability of MgO to stabilize iridium under oxidizing conditions is in line with the known inability of MgO to form an iridate.

The oxidative stabilization of 2.9 wt. % iridium catalysts on BaO/$\eta$-Al$_2$O$_3$ supports has been found to be highly dependent upon the concentration of BaO. This effect is clearly shown in FIG. 1. In this study, a series of 0.15 mmoles iridium/g catalysts (2.9%) were subjected to oxidation treatments using 20% in He at 500° C. for 4.0 hours. The ability of BaO/$\eta$-Al$_2$O$_3$ supports to retard the oxidative agglomeration of iridium was compared against a 2.9% iridium/$\eta$-Al$_2$O$_3$ catalyst. The quantity of BaO was varied from 0.0 to 0.75 mmoles/g of catalyst in increments of 0.15 mmoles. FIG. 1 shows that as soon as the acid sites of $\eta$-Al$_2$O$_3$ are titrated with basic BaO, stabilization of iridium rapidly ensues. $\eta$-Al$_2$O$_3$ possesses 0.30 ± 0.05 mmoles of acid sites/g as determined by $\eta$-butylamine titration employing a series of Hammett indicators. The results summarized in FIG. 1 further suggest that BaO first must react with the support acidic sites. The strength of the support acid-Group IIA oxide base interaction does not allow BaO to simultaneously interact with iridium to produce a stable BaIrO$_3$ species. Not until the BaO concentration is in excess of that of the $\eta$-Al$_2$O$_3$ acid sites does stabilization of iridium take place. This hypothesis is verified in the case of a BaO/SiO$_2$ support which imparts iridium stabilization upon the first introduction of BaO. This results since SiO$_2$ is nonacidic and does not consume BaO by an acid-base interaction; therefore, BaO is readily available to interact with and stabilize the iridium component.

The importance of this finding is that in hydrocarbon conversion reactions requiring bifunctional catalysts (metal and acid components) an acidic component must be mixed with the nonacidic oxidatively stabilized metal component to obtain an overall acidic catalyst.

EXAMPLE 3 — Platinum Catalysts

In a clean 25 ml graduate cylinder equipped with a nitrogen purge system was placed 1.94 g of Ba(NO$_2$)$_2$.H$_2$O. To the barium salt was added 2.0 ml of a standard chloroplatinic acid solution (0.10 g Pt/ml); a brown gas (N$_2$O$_3$) was given off. After gas evolution had ceased, the solution volume was adjusted to 5.7 ml by the addition of distilled water. This solution was used to impregnate 8.8 g of $\eta$-Al$_2$O$_3$. The catalyst was dried overnight at 130° C., and the dry catalyst was then calcined at 550° C. for 4.0 hours under 20% O$_2$ in He flowing at 500 cc/min. The resulting catalyst contained 11.5 wt. % BaO and 1.92 wt. % Pt supported on $\eta$-Al$_2$O$_3$.

The BaO stabilized platinum catalyst, along with a 1.92% Pt/$\eta$-Al$_2$O$_3$ catalyst, was calcined at 710° C. for 2.5 hours under 20% O$_2$ in He flowing at 500 cc/min. This severe treatment badly agglomerated the platinum component in the case of the 2% Pt/$\eta$-Al$_2$O$_3$ catalyst, whereas the BaO stabilized 2% Pt/$\eta$-Al$_2$O$_3$ did not exhibit any x-ray diffraction lines due to platinum metal. This result suggests that the platinum crystallite size in the BaO stabilized catalyst is less than 50 Å. In the calcined 2% Pt/$\eta$-Al$_2$O$_3$ catalyst the average crystallite size of the agglomerated platinum component was estimated from the x-ray diffraction data to be about 330 Å.

This study clearly shows that platinum, like iridium, can be stabilized against oxidative agglomeration in the presence of BaO. The mechanism of stabilization is presumably via the formation of a stable complex oxide surface phase such as BaPt$_3$O$_4$. An active platinum metal surface phase is readily generated by H$_2$ reduction at 500° C.

Alternatively, oxidatively stable Group IIA metal oxide-platinum catalysts can be prepared by the impregnation of platinum solutions onto preformed supports such as BaO/Al$_2$O$_3$, SrO/Al$_2$O$_3$, CaO/Al$_2$O$_3$, BaO/SiO$_2$, SrO/SiO-Al$_2$O$_3$, etc. In the case of acidic carriers such as Al$_2$O$_3$ and SiOAl$_2$O$_3$, the concentration of the Group IIA metal oxide must exceed the acidity of the carrier before platinum stabilization ensues.

EXAMPLE 4 — Nickel Catalysts

A 2.0% Ni/$\eta$-Al$_2$O$_3$ catalyst was prepared by impregnating 9.8 of $\eta$-Al$_2$O$_3$ with a solution containing 2.0 ml of a standard nickel nitrate solution (0.10 g Ni/ml) diluted to 6.0 ml with distilled water. The catalyst was dried overnight at 130° C. H$_2$ chemisorption, as described below, showed the nickel component to be 14.8% dispersed.

A 2.0% Ni, 11.9% BaO$\eta$-Al$_2$O$_3$ catalyst was prepared by impregnating 9.8 g of a 11.9% BaO/$\eta$-Al$_2$O$_3$ support with a solution containing 2.0 ml of a standard nickel nitrate solution (0.10 g Ni/ml) diluted to 5.7 ml with distilled water. The catalyst was dried overnight at 130° C. H$_2$ chemisorption showed the nickel component to be 18.3% dispersed.

The above 2% Ni/$\eta$-Al$_2$O$_3$ and 2% Ni/11.9% BaO/$\eta$-Al$_2$O$_3$ were subjected to a calcination treatment at 450° C. for 4.0 hours under 20% O$_2$ in He flowing at 500 cc/min. Following this treatment the nickel dispersion defined as the ratio of number of surface nickel atoms to the total number of Ni atoms in the sample times 100 was determined by selective hydrogen chemisorption. A hydrogen isotherm was determined for each sample at room temperature and the amount of hydrogen adsorbed when all the surface nickel atoms are covered with hydrogen was determined by extrapolating the linear flat portion of the isotherm to zero pressure. The dispersion is then determined from the number of hydrogen atoms adsorbed at monolayer coverage times 100 divided by the total number of nickel atoms in the sample. The dispersion of the calcined 2%Ni/η-Al$_2$O$_3$ sample determined in this manner was 7% while the BaO stabilized sample maintained a dispersion of 16%. These results clearly show that the agglomeration of nickel can be completely suppressed when oxidation is carried out in the presence of BaO. Oxidative stabilization is presumably achieved via the formation of a complex oxide surface species such as BaNiO$_2$. Upon reduction, the chemisorption data clearly indicates that the complex oxide phase formed under oxidizing conditions is broken down and liberates nickel metal and a BaO surface phase.

EXAMPLE 5 — Palladium Catalysts 9.9 g of a 0.52 mmole (7.9%) BaO/η-Al$_2$O$_3$ was impregnated with a solution containing 1.11 ml of a standard palladium chloride solution (0.0992 g Pd/ml) diluted to 6.4 ml. The catalyst was dried overnight at 120° C. The resulting 1.1% Pd catalysts have a BaO/Pd mole ratio of 5.

This catalyst was reduced at 500° C. under 20% H$_2$ in He (500 cc/min) for 1.0 hour and then calcined at 600° C. under 20% in He (500 cc/min) for 4.0 hours. An x-ray diffraction pattern of the calcined catalyst did not exhibit any Pd oxide or Pd metal X-ray diffraction lines which would be indicative of palladium agglomeration.

EXAMPLE 6 — Rhodium Catalysts 200 g of extruded Al$_2$O$_3$ (178 m$^2$/g) was impregnated with a 130 ml aqueous solution containing 27.8 g of Ba(NO$_2$)$_2$.H$_2$O. The barium doped extrudate was dried at 130° C. for 5.0 hours and then calcined at 600° C. under flowing dry air overnight. The resulting support contains 8.0 wt. % BaO. The BET surface area of the BaO/Al$_2$O$_3$ support was found to be 167 m$^2$/g.

To 198 g of the 8.0% BaO/Al$_2$O$_3$ carrier was added a 180 ml solution of 5.02 g of RhCl$_3$ in distilled water. After allowing the RhCl$_3$ solution to contact the BaO-/Al$_2$O$_3$ carrier overnight the catalyst was dried at 130° C. for 4.0 hours and then calcined at 280° C. overnight under flowing dry air. The resulting catalyst contains 1.0% Rh, 8.0% BaO by weight on the extruded Al$_2$O$_3$ carrier.

The rhodium component in the fresh catalyst was found to be 46% dispersed by a H$_2$ chemisorption measurement. After subjecting the catalyst to a calcination treatment at 600° C. for 4.0 hours under 20% O$_2$ in He flowing at 500 cc/min, the catalyst maintained a rhodium dispersion level of 50%. This result suggests that rhodium may be protected from undergoing oxidative agglomeration in the presence of BaO (or CaO or SrO). The mode of stabilization may be through the formation of a surface complex oxide such as BaRh$_2$O$_4$ which does not agglomerate under oxidizing conditions.

EXAMPLE 7 — Platinum and Iridium Bimetallic Catalysts

Homogeneous Impregnation of Barium, Platinum and Iridium

In a 50 graduate cylinder equipped with a nitrogen purge system was placed 9.7 g of Ba(NO$_2$)$_2$.H$_2$O. To the barium salt was added 8.0 ml of distilled water. To the saturated Ba(NO$_2$)$_2$ solution was added 10.0 ml of a standard chloroplatinic acid solution (0.10 g Pt/ml). A dark brown gas (N$_2$O$_3$) was given off. After gas evolution had ceased, 9.2 ml of a standard chloroiridic acid solution (0.109 g Ir/ml) was added. Again a dark brown gas N$_2$O$_3$ was given off. After gas evolution was complete, the solution volume was adjusted to 29 ml by the addition of distilled water. The resultant light orange solution was used to impregnate 44 g of η-Al$_2$O$_3$. The catalyst was dried overnight at 130° C. and then calcined at 500° C. for 4.0 hours under 20% in He flowing at 500 cc/min. The final catalyst contains by wt. % 11.1% BaO, 1.85% Pt and 1.85% Ir. An x-ray diffraction pattern of the final catalyst was devoid of any lines due to platinum or iridium oxide.

Comparable platinum and iridium BaO doped catalysts may also be prepared as follows:

EXAMPLE 8 — Sequential Impregnation of Iridium and Platinum

A barium oxide support containing 11.8% BaO/η-Al$_2$O$_3$ was prepared by impregnating 9.0 g of η-Al$_2$O$_3$ with a solution of 1.94 g of Ba(NO$_2$)$_2$.H$_2$O dissolved in 5.8 ml of distilled water. After drying overnight at 120° C., the support was calcined at 600° C. under flowing air for 16 hours to ensure complete formation of a BaO surface phase. To 3.84 g of the 11.8% BaO/η-Al$_2$O$_3$ support was added 0.78 ml of a standard chloroiridic solution (0.103 g Ir/ml) diluted to 2.2 ml with distilled water. The iridium containing catalyst was dried overnight at 120° C. and then heated to 260° C. under flowing air for 4.0 hours. After the drying procedure the platinum component was placed on the support by impregnating the iridium containing catalyst with 0.82 ml of a standard chloroplatinic acid solution (0.0975 g Pt/ml) diluted to 2.2 ml with distilled water. The final catalyst after drying at 120° C. overnight and further drying at 260° C. for 4.0 hours under flowing air contains 10.9% BaO, 1.92% Pt and 1.92% Ir supported on η-Al$_2$O$_3$.

The impregnation sequence of the platinum and iridium components can be reversed without causing any change in the stabilization properties of the final catalyst.

EXAMPLE 9 — Coimpregnation of Iridium and Platinum 3.84 g of a 11.8% BaO/η-Al$_2$O$_3$ carrier was impregnated with a solution containing 0.78 ml of a standard chloroiridic solution (0.103 g Ir/ml) and 0.82 ml of a standard chloroplatinic acid solution (0.0975 g Pt/m) diluted to 2.2 ml with distilled water. The final catalyst after drying overnight at 120° C. and then further drying at 260° C. for 4.0 hours under flowing air contains 10.9% BaO, 1.92% Pt and 1.92% Ir supported on η-Al$_2$O$_3$.

EXAMPLE 10 — Comparison of Catalyst Preparation Techniques

A series of 2% Pt, 2% Ir bimetallic catalysts supported on η-Al$_2$O$_3$ containing varying amounts of a BaO stabilizer was prepared by one or more of the three methods (Examples 7, 8 and 9) described above. The oxidative stability of these catalysts were compared against a 2% Pt, 2% Ir/η-Al$_2$O$_3$ catalyst. The catalysts were subjected to the following treatment: reduction at 500° C. under 20% H$_2$ in He (500 cc/min) for 1.0 hour followed by calcining at 500° C. for 4.0 hours under 20% O$_2$ in He (500 cc/min). The relative metal agglomeration (Ir component) in these catalysts was determined by comparative x-ray diffraction measurements. The results of these tests are presented in Table III.

Table III

Oxidative Stability Tests[a] of 2% Pt, 2% Ir Bimetallic Catalysts

| Wt. % BaO | Impregnation Technique | (%) Relative Agglomeration |
|---|---|---|
| 0.0 | Coimpregnation | 100 |
| 7.9 | Coimpregnation | 0.0 |
| 7.9 | Sequential | 0.0 |
| 9.9 | Coimpregnation | 0.0 |
| 9.9 | Sequential | 0.0 |
| 11.8 | Homogeneous (Ex. 7) | 0.0 |
| 11.8 | Coimpregnation (Ex. 9) | 0.0 |
| 11.8 | Sequential (Ex. 8) | 0.0 |
| 11.8[b] | Homogeneous | 0.0 |
| 11.8[b] | Coimpregnation | <10 |
| 11.8[b] | Sequential | 0.0 |

[a] Catalysts were reduced at 500° C. under 20% $H_2$ in He and then calcined under 20% $O_2$ in He at 500° C. for 4.0 hours.
[b] Reduction-oxidation cycle repeated a second time.

Through one reduction-oxidation cycle the BaO doped PtIr catalysts all display complete stabilization. However, a second reduction-oxidation cycle causes the catalyst prepared by coimpregnating Pt and Ir onto a BaO/$Al_2O_3$ support to experience some agglomeration. Catalysts prepared either by impregnation with the homogeneous method described above or a sequential impregnation of Pt and Ir onto a preformed BaO/$\eta$-$Al_2O_3$ carrier can be recycled through numerous reduction-oxidation sequences without undergoing metal agglomeration.

EXAMPLE 11 — Bifunctional Catalysts

Bifunctional catalysis requires the mutual participation of two catalyst functions, namely an acidic component and a metal component. Since the oxidative stabilization of supported Group VIII metals by Group IIA metal oxides results in the neutralization of the acidic function of common acidic supports such as $Al_2O_3$ and SiO-$Al_2O_3$ a technique for reestablishing overall catalyst acidity is required. This has been accomplished by physically mixing an acidic component with the non-acidic Group IIA metal oxide-Group VIII metal (or metals) component. This approach is exemplified by the following preparation:

2.0 g of a 1.85% Pt, 1.85% Ir, 11.1% BaO/$\eta$-$Al_2O_3$ catalyst which was calcined at 550° C. for 4.0 hours under 20% $O_2$ in He (500 cc/min) was diluted to a total of 12.3 g by the addition of 10.3 of a chlorided $\eta$-$Al_2O_3$ (0.7% Cl). The physical mixture was ball milled for 2.0 hours. The resulting physically mixed catalyst contains an effective metal loading of 0.3% Pt, 0.3% Ir and 1.8% BaO.

The ability of the metal dispersion of a 0.3% Pt, 0.3 Ir/$Al_2O_3$ catalyst to withstand a high temperature oxidation was compared with a 0.3 Pt, 0.3% Ir, 1.8% Ba/$Al_2O_3$ catalyst prepared by the method described in the preceding paragraph. Each sample was calcined in 2% $O_2$ in He for 4 hours at each of the temperatures from 200° to 600° C., reduced in hydrogen 1 hour at 500° C., and evacuated 1/2 hour at 450° C. The hydrogen isotherm was determined at room temperature on the evacuated catalysts and the amount of hydrogen adsorbed by the metals in the catalysts was determined from the zero pressure intercept of the linear, flat portion of the isotherm. Since hydrogen adsorption occurs only on the surface metal atoms the percentage of metal atoms in the sample which are surface atoms, called the dispersion, can be determined. Data on the degree of metal dispersion along with values of the metal surface area derived from the hydrogen chemisorption date are given in the following table.

Table V

Metal Dispersion of Pt-Ir Samples as a Function of Oxidation Temperature

| Catalyst | 260° C. | 500° C. | 550° C. | 600° C. |
|---|---|---|---|---|
| 0.3% Pt, 0.3% Ir-$Al_2O_3$ | | | | |
| Metal Dispersion, % | 87 | 55 | 39 | 23 |
| Metal Surface Area, $m^2$/g | 206 | 130 | 92 | 55 |
| 0.3% Pt, 0.3% Ir, 1.8% BaO-$Al_2O_3$ | | | | |
| Metal Dispersion, % | 74 | 100 | 100 | 58 |
| Metal Surface Area, $m^2$/g | 175 | 237 | 237 | 137 |

A metal dispersion of 100% corresponds to a metal surface area of 237 $m^2$/g. The activity of Pt-Ir catalysts is proportional to the metal surface area at a given chloride level. Thus, the 0.3% Pt, 0.3% Ir, 1.8 BaO/$Al_2O_3$ catalyst will actually increase in activity on oxidation at 500° C. and will have a higher activity than the 0.3% Pt, 0.3% Ir/$Al_2O_3$ catalyst for oxidation temperatures up to and through 600° C.

EXAMPLE 12 — Redispersion of Agglomerated Catalysts

It has been found that Group IIA metal oxide/$\eta$-$Al_2O_3$ not only suppresses oxidative agglomeration of iridium catalysts but also can lead to redispersion of agglomerated iridium catalysts under high temperature treatments in an oxygen containing atmosphere. Iridium redispersion was ascertained in the following manner: a 1% iridium/$\eta$-$Al_2O_3$ catalyst was partially agglomerated by calcining at 500° C. under 20% $O_2$ in He (500 cc/min) for 1.0 hour. Following this treatment, the iridium component was found to be 69% dispersed by a $H_2$ chemisorption measurement. The partially agglomerated (69% dispersed) 1% iridium catalyst was impregnated with a Ba($NO_2$)$_2$ solution so as to obtain a catalyst having a Ba/iridium ratio of 15. The resulting Ba doped iridium catalyst was then calcined at 600° C. under 20% $O_2$ in He (500 cc/min) for 6.0 hours. $H_2$ chemisorption showed the 600° C. calcined catalyst to have a 95% dispersed iridium component. This experiment indicates that redispersion of an agglomerated iridium crystallite can be affected by capturing mobile iridium species (generated by high temperature oxygen treatment) with a surface chemical trap, namely BaO, which combines with a mobile iridium species to form an oxidatively stable Ba$IrO_3$ surface species. Upon reduction the Ba$IrO_3$ surface species liberates a well dispersed active iridium metal phase and regenerates BaO which can be reused in any subsequent oxidation treatments.

Catalytic Studies

EXAMPLE 13 — n-Heptane Dehydrocyclization

Figure 2:
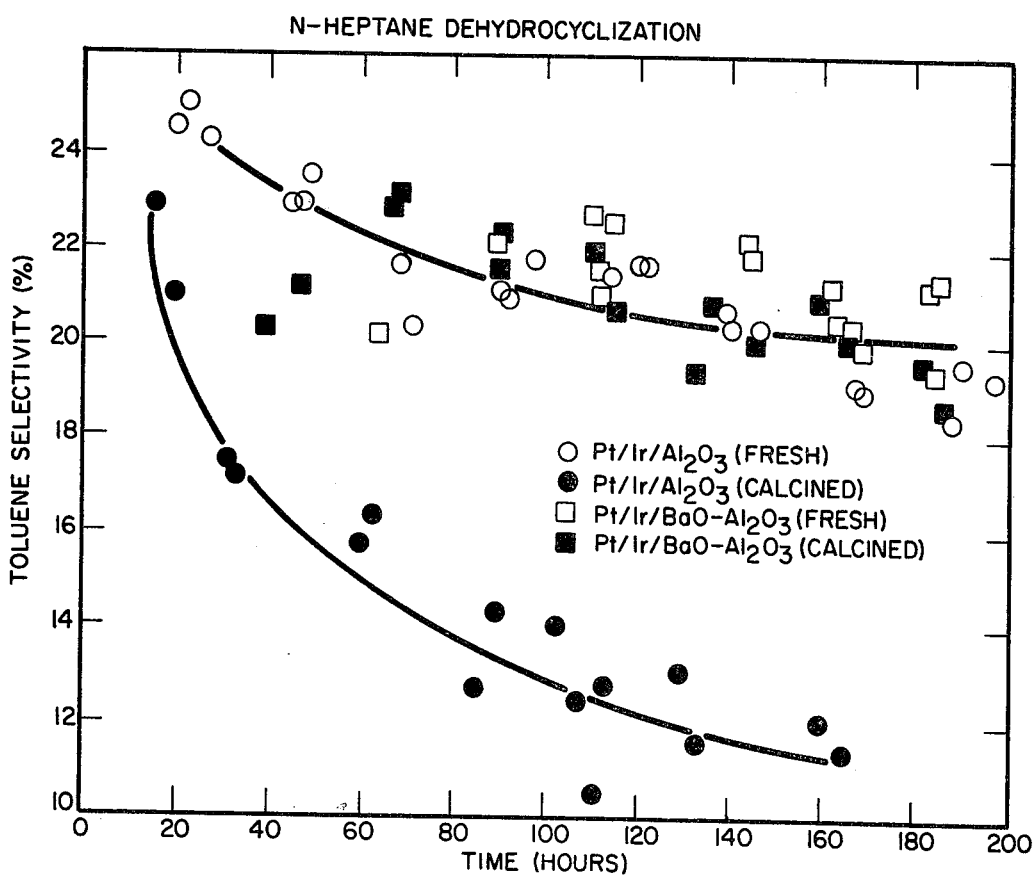
FIG. 2 shows the improvement in toluene selectivity of the instant catalysts compared to prior art catalysts versus time.

The n-heptane dehydrocyclization activity of a physically mixed 0.3% Pt, 0.3% Ir, 1.8% BaO/$\eta$-$Al_2O_3$ catalyst has been compared with a 0.3% Pt, 0.3% Ir/$Al_2O_3$ catalyst. The n-heptane dehydrocyclization experiments were carried out at 482° C., 200 psig, w/hr/w = 21.4, and a $H_2$/n-heptane mole ratio of 5.6 The results of these comparative experiments are summarized in FIG. 2 which displays a (%) Toluene Selectivity versus Time plot. It is seen that the toluene selectivity of the fresh Pt, Ir/$Al_2O_3$ and Pt, Ir, BaO/$Al_2O_3$ catalysts are comparable. This indicates that the bifunctional activity of the physically mixed catalyst is equivalent to that of a catalyst containing the acidic and metal components on the same catalyst particle. After regenerating [calcining in 20% $O_2$ in He (500 cc/min) for 4.0 hours at 500° C.] the spent Pt, Ir/$Al_2O_3$ catalyst, the toluene selectivity drops off drastically from that demonstrated by the fresh catalyst. This fall off in toluene selectivity is the result of the agglomeration of the iridium component which occurred during the oxygen calcination. The regenerated [calcined at 500° C. under 20% $O_2$ in He (500 cc/min) for 4.0 hours] spent Pt, Ir, BaO/$Al_2O_3$ catalyst in contrast maintains its high initial toluene selectivity. This indicates that the iridium component remains well dispersed and in an active state.

The results of these n-heptane dehydrocyclization experiments are striking since they clearly demonstrate that an iridium containing catalyst in the presence of a Group IIA metal oxide can be protected against agglomeration. It is further established that the protected metal components do not suffer a loss in catalytic activity.

EXAMPLE 14 — Naphtha Reforming

Figure 3:
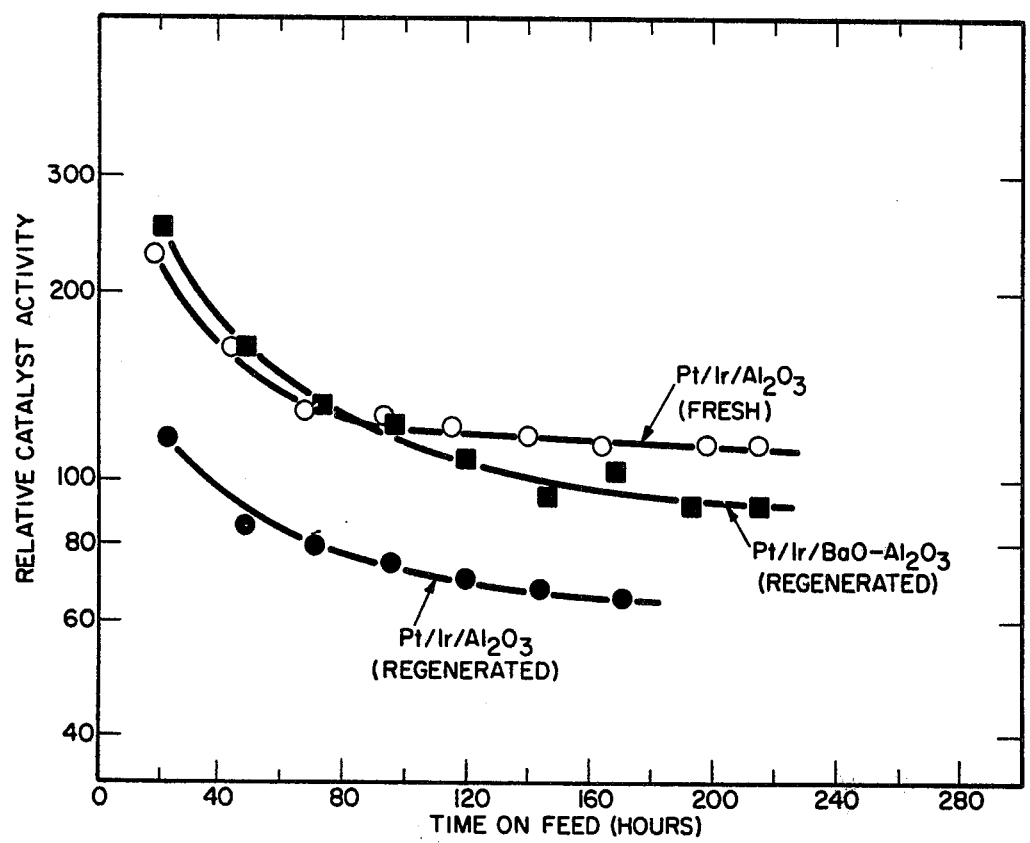
FIG. 3 displays the relative catalyst activity of a prior art catalyst (fresh and regenerated) compared to a catalyst of the instant invention versus time.

The naphtha reforming ability of a physically mixed 0.3% Pt, 0.3% Ir, 1.8% BaO/$Al_2O_3$ catalyst has been compared with a 0.3% Pt, 0.3% Ir/$Al_2O_3$ catalyst. The naphtha reforming experiments were carried out on a Bayway naphtha containing 0.5 ppm sulfur. The reforming experiments were carried out at 485°–490° C., 200 psig, a w/hr/w = 2.1, and 6000 SCF $H_2$/BBL. The catalysts were presulfided to breakthrough using 1% $H_2S$ in $H_2$ before placing them on oil. The results of these comparative naphtha reforming runs are summarized in FIG. 3 which displays a relative catalyst activity versus time plot. The fresh Pt, Ir/$Al_2O_3$ catalyst lines out at a relative catalyst activity of about 115 after 80 hours in feed. After regenerating (calcining the spent catalyst at 471° C. under 2% $O_2$ in He flowing at 500 cc/min for 2.0 hours), the burned catalyst drops to a relative catalyst activity of about 70 after 80 hours on feed. This large drop in catalyst activity is the result of agglomeration of the iridium component which greatly diminishes the surface concentration of the active iridium component. The agglomeration of the iridium component was verified by x-ray diffraction measurements on the recovered, spent Pt, Ir/$Al_2O_3$ catalyst.

After regenerating (calcining at 471° C. under 2% $O_2$ in He flowing at 500 cc/min for 2.0 hours) a spent (380 hours on feed) Pt, Ir, BaO/$\eta$-$Al_2O_3$ catalyst, a lined out relative activity of about 100 was obtained after 120 hours on feed. During the first 120 hours on feed the regenerated BaO stabilized catalyst demonstrates a relative catalyst activity comparable with that given by a fresh Pt, Ir/$Al_2O_3$ reforming catalyst. The high initial activity maintenance suggests the use of the catalyst in a cyclic reforming operation. The spent, regenerated Pt, Ir, BaO/$\eta$-$Al_2O_3$ was devoid of any x-ray diffraction lines due to iridium metal. Thus, the iridium component is completely protected from oxidative agglomeration in the presence of BaO.

The results of these naphtha reforming runs clearly demonstrate the regenerability of iridium catalysts in the presence of a Group IIA metal oxide such as BaO. It was further established that a physical mixture of an acid component and an oxidatively stable, nonacidic metal component gives a bifunctional reforming activity comparable with that of a catalyst containing the acidic and metal components on the same catalyst particle.

What is claimed is:

1. A reforming process which comprises contacting a naphtha feedstream with a catalyst at reforming conditions and recovering a higher octane product which catalyst comprises a Group VIII metal or mixtures thereof supported on a Group IIA metal oxide selected from the group consisting of calcium oxide, barium oxide, strontium oxide and mixtures thereof which Group IIA metal oxide is supported on an acidic refractory oxide wherein the Group IIA metal oxide is present in sufficient quantity to neutralize the sites of the acidic refractory oxide support and to supply an excess at a level of from about 0.5 to 50 moles Group IIA metal oxide per mole of said Group VIII metal or mixtures thereof, the Group VIII metal or mixtures thereof on Group IIA metal oxide or mixtures thereof on neutralized acidic refractory oxide combination being admixed with an acidic refractory oxide.

2. A reforming process which comprises contacting a naphtha feedstream with a catalyst at reforming conditions and recovering a higher octane product which catalyst comprises a Group VIII metal or mixtures thereof in combination with a Group IIA metal oxide selected from the group consisting of calcium oxide, barium oxide, strontium oxide and mixtures thereof supported on a nonacidic refractory oxide support, the Group IIA metal oxide being present at a level of from about 0.5 to 50 moles per mole of said Group VIII metal and mixtures thereof, the combination being admixed with an acidic refractory oxide.

3. A reforming process which comprises contacting a naphtha feedstream with a catalyst at reforming conditions and recovering a higher octane product, which catalyst comprises a Group VIII metal or mixture thereof supported on a Group IIA metal oxide selected from the group consisting of calcium oxide, barium oxide, strontium oxide and mixtures thereof which Group IIA metal oxide is supported on an acidic refractory oxide which has been neutralized with MgO, wherein the Group IIA metal oxide selected from the group consisting of calcium oxide, barium oxide, strontium oxide and mixtures thereof is present at a level of from about 0.5 to 50 moles Group IIA metal oxide per mole of said Group VIII metal or mixture thereof, the Group VIII metal or mixture thereof or Group IIA metal oxide or mixture thereof on MgO neutralized acidic refractory oxide combination being admixed with an acidic refractory oxide.

4. The process of claims 1, 2 or 3 wherein the Group VIII metal or mixture thereof is selected from the Group VIII noble metals.

5. The process of claims 1, 2 or 3 wherein the Group VIII metal or mixture thereof is selected from the group consisting of platinum and iridium.

6. The process of claim 4 wherein said noble metal comprises from 0.01 to 2% by weight of said catalyst.

7. The process of claims 1, 2 or 3 wherein said acidic refractory oxide is selected from the group consisting of zeolite, alumina, halogen treated alumina and silica-alumina.

8. The process of claims 1, 2 or 3 further including periodically regenerating said catalyst after said catalyst has been deactivated by the deposition of carbon on the active sites thereof by contacting with oxygen at a temperature of at least 400° C. for a time sufficient to remove said carbon and with hydrogen at a temperature of from 200 to 700° C., a pressure of 15 to 500 psig, for a time sufficient to substantially reduce all the Group VIII metal to the metallic state.

* * * * *